(12) United States Patent
Marcos Munoz

(10) Patent No.: US 9,504,382 B2
(45) Date of Patent: Nov. 29, 2016

(54) PIECE OF APPARATUS FOR MEASURING THE TOPOGRAPHY AND THICKNESS OF THE CORNEA AND A MEASURING METHOD EMPLOYED TO THIS END

(71) Applicant: Davalor Consultoria Estrategica y Tecnologica, S.L., Gorraiz (Navarra) (ES)

(72) Inventor: Juan Jose Marcos Munoz, Gorraiz (Navarra) (ES)

(73) Assignee: DAVALOR CONSULTORIA ESTRATEGICA Y TECNOLOGICA, S.L., Gorraiz (Navarra) (ES)

(*) Notice: Subject to any disclaimer, the term of this patent is extended or adjusted under 35 U.S.C. 154(b) by 12 days.

(21) Appl. No.: 14/415,921

(22) PCT Filed: Jul. 3, 2013

(86) PCT No.: PCT/ES2013/070467
§ 371 (c)(1),
(2) Date: Jan. 20, 2015

(87) PCT Pub. No.: WO2014/101645
PCT Pub. Date: Jan. 30, 2014

(65) Prior Publication Data
US 2015/0173610 A1    Jun. 25, 2015

(30) Foreign Application Priority Data

Jul. 25, 2012    (ES) .................................. 201231191

(51) Int. Cl.
*A61B 3/107* (2006.01)
*A61B 3/10* (2006.01)
(Continued)

(52) U.S. Cl.
CPC ........... *A61B 3/1005* (2013.01); *A61B 3/0008* (2013.01); *A61B 3/107* (2013.01); *A61B 3/113* (2013.01)

(58) Field of Classification Search
CPC .. A61B 3/1005; A61B 3/107; A61B 3/0008; A61B 3/113; A61B 3/10; A61B 3/00

USPC .................................................. 351/206, 209
See application file for complete search history.

(56) References Cited

U.S. PATENT DOCUMENTS 5,204,703 A    4/1993 Hutchinson et al.
2003/0123027 A1    7/2003 Amir et al.
(Continued)

FOREIGN PATENT DOCUMENTS

DE    10 2008008732 A    8/2009
EP         2168474 A    3/2010
(Continued)

OTHER PUBLICATIONS

IPRP/Written Opinion dated Feb. 5, 2015 along with the English translation thereof for the PCT Application No. PCT/ES2013/070467.

*Primary Examiner* — Euncha Cherry
(74) *Attorney, Agent, or Firm* — Lucas & Mercanti, LLP

(57) ABSTRACT

A piece of apparatus for measuring the topography and thickness of the cornea and a measuring method employed to this end, this piece of apparatus comprising a system for tracking (1) the direction of gaze (D) of the eyes (2), which includes a camera (6) and a diffuse light emitter (7) for each eye (2); a system for inspecting (3) the cornea (4), which comprises a light emitter (8) for each eye (2) and emits light beams (9) onto the cornea (4) and a receiver assembly (10), which receives the light reflected by the cornea (4); a system for displaying visual stimuli (13) in front of the eyes (2) and; a computer (5) that controls the light emitters (7, 8) and the system for displaying visual stimuli (13), which also processes the information from each camera (6) and the receiver assembly (10), in order to determine the topography and thickness of the cornea (4) of each eye (2).

23 Claims, 2 Drawing Sheets

(51) Int. Cl.
*A61B 3/113* (2006.01)
*A61B 3/00* (2006.01)

(56) References Cited

U.S. PATENT DOCUMENTS

2009/0135372 A1 5/2009 Sarver
2009/0275929 A1* 11/2009 Zickler .................. A61B 3/113
351/206
2012/0147328 A1 6/2012 Yahav

FOREIGN PATENT DOCUMENTS

WO WO2009/127442 A 10/2009
WO WO2012/067508 A 5/2012

* cited by examiner

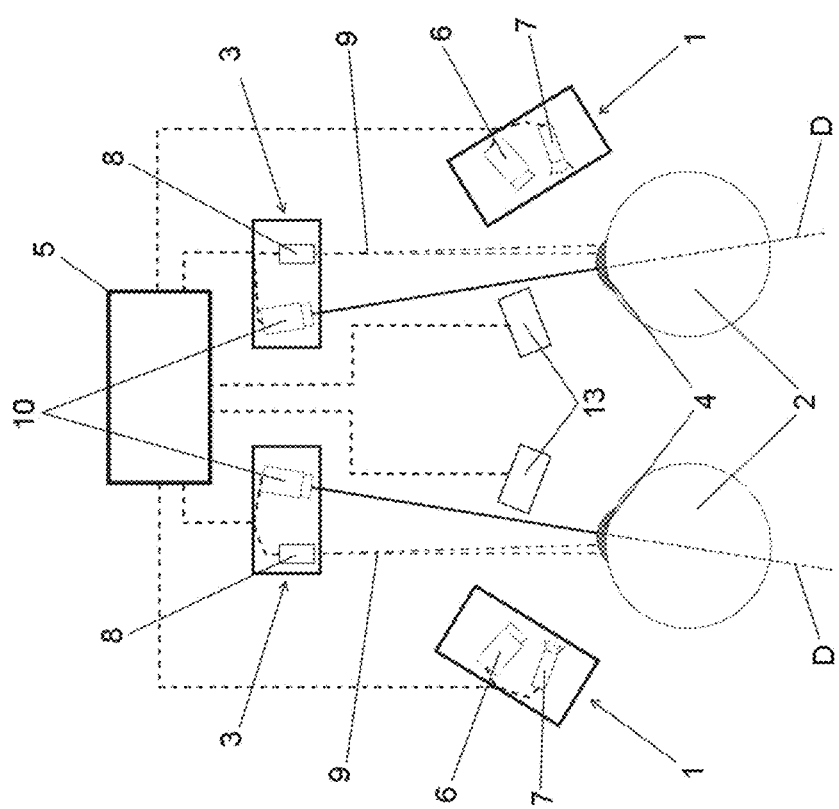

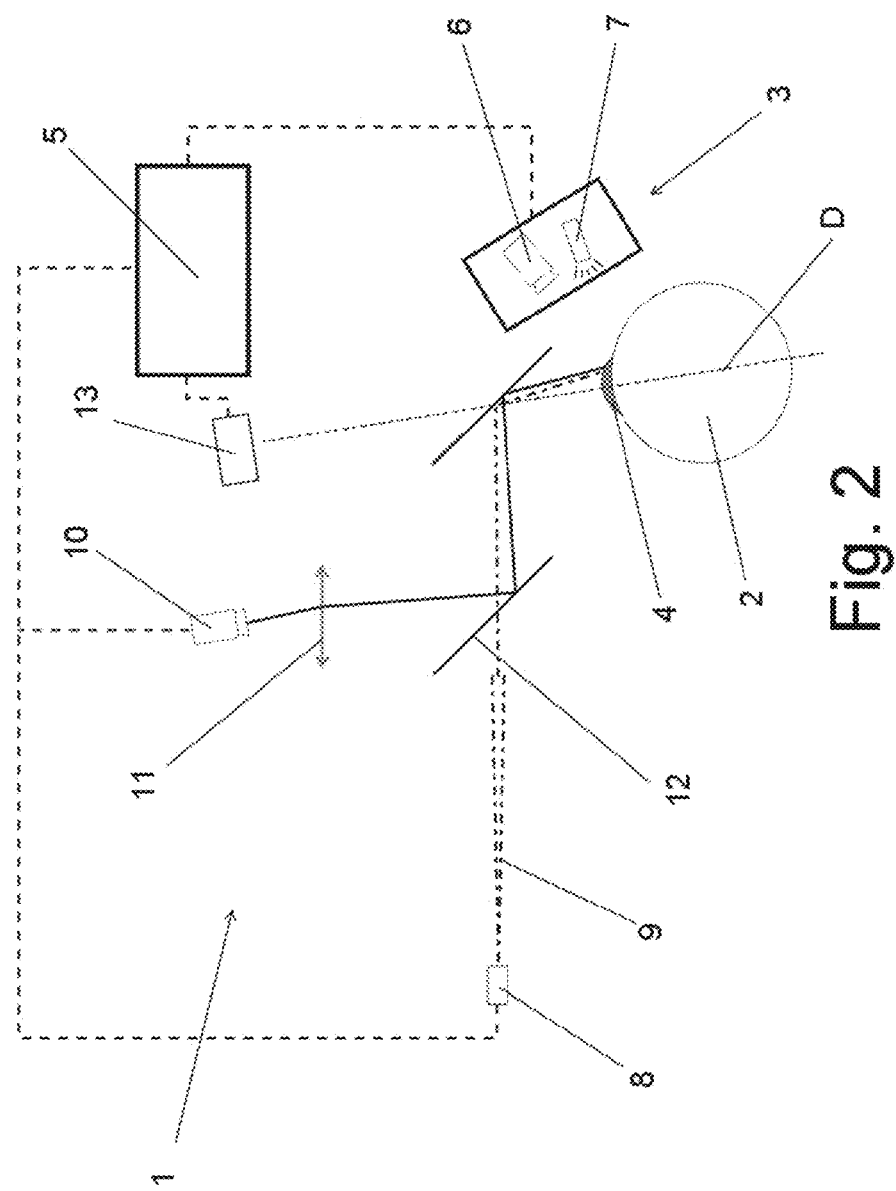

PIECE OF APPARATUS FOR MEASURING THE TOPOGRAPHY AND THICKNESS OF THE CORNEA AND A MEASURING METHOD EMPLOYED TO THIS END

CROSS REFERENCE TO RELATED APPLICATION

This Application is a 371 of PCT/ES2013/070467 filed on Jul. 3, 2013 which, in turn, claimed the priority of Spanish Patent Application No. P201231191 filed on Jul. 25, 2012, both applications are incorporated herein by reference.

TECHNICAL FIELD OF THE INVENTION

The present invention relates to devices and methods used to determine optical characteristics of the eye, proposing a piece of apparatus and a method for measuring the topography and thickness of the cornea.

STATE OF THE ART

Sight is the gateway for 95% of the information we receive and, therefore, the most important route for spatial orientation, emotional communication and particularly, learning (for example, in relation to formal recognition, reading and reading comprehension skills, etc.). As such, it is advisable to check vision regularly, in order to detect and treat functional problems that may arise.

The cornea is a transparent, hemispherical structure located at the front of the eye, serving to protect the iris and lens, whilst enabling light to pass through. Its refractive properties determine ⅔ of the human eye's ability to focus. Corneal dioptric power results from refraction of the anterior surface of the cornea, thus meaning the refractive power of the cornea largely corresponds to the shape of its surface, represented by the topography thereof.

Measuring the topography of the cornea and the thickness thereof (the difference between the outer layer and the inner layer of the cornea) makes it possible to recognise conditions such as astigmatisms, myopia or hypermetropia, corneal ectasias such as keratoconus, keratoglobus and allergic conjunctivitis, in order to evaluate the conditions of the cornea prior to surgical treatments for cataracts, keratomileusis or personalised refractive surgery, or to study and fit contact lenses, etc.

Conventional cornea examination devices tends to be expensive, with high technical performance and high resolution, essentially being used to detect significant alterations of the cornea or for analysis before eye surgery. Furthermore, in order to measure the cornea, these devices require the patient to keep the direction of the gaze of their eyes fixed on a certain point, since, in order to be able to carry out the test, it is essential that the measuring system is correctly aligned and focused relative to the eye to be analysed, this potentially proving irritating and tedious for the patient, it being necessary to repeat the test in many cases, owing to the patient blinking or looking away from the point indicated. As a result, despite the significant prevalence of corneal problems, most of the population is unaware of the condition their cornea is in.

Therefore, a low cost piece of apparatus for measuring the topography and thickness of the cornea becomes necessary, which may be more accessible to users and even enable the patient to carry out the test themselves, in order to determine whether or not their cornea is normal or if they have problems.

Object of the Invention

In accordance with the present invention, a piece of apparatus and a method that enable the topography and thickness of the cornea to be measured, regardless of the area in which the patient's gaze may divert, is proposed, in such a way that the irritation and discomfort of conventional solutions is avoided.

The apparatus for measuring the topography and thickness of the cornea is made up of a system for tracking the direction of gaze of the patient's eyes, a system for inspecting the cornea, a system for displaying visual stimuli in front of the patient's eyes and a computer functionally connected to said system for determining the topography and thickness of the cornea of each eye. The tracking system makes it possible to know which direction the patient's is pointing, in such a way that the inspection system may collect data on the cornea, regardless of the area in which the patient is fixing the direction of their gaze.

The system for displaying visual stimuli in front of the patient's eyes may be formed by a number of screens, upon which optotypes or visual stimuli are displayed, which make it possible to stimulate and guide the direction of the patient's gaze, in order to expose different areas of the cornea, in such a way that the inspection system may be provided with a greater area of cornea from which to obtain information. Moreover, the possibility of the system displaying visual stimuli has been put forward in the form of four LEDs positioned at strategic points close to the inner peripheral portion of the visual field of the patient's eyes, in such a way that, via the selective emission of light from these LEDs, it is possible to stimulate and guide the direction of the patient's gaze.

The system for tracking the direction of gaze of the patient's eyes is formed by an emitter for each eye, which emits diffuse light in order to illuminate the cornea and, a camera linked to each eye, with which reflections of the diffuse light emitted are observed. The inspection system is likewise made up of a light emitter for each eye, which emits light beams onto the cornea, and a receiver assembly, which receives the light reflected by the cornea. As such, the computer controls the light emitters and processes the information from each camera and the receiver assembly to determine the topography and the thickness of the cornea of each eye.

The receiver assembly that receives light reflected by the cornea is formed by a single receiver element common to both eyes, a set of directed mirrors being used to direct the light reflected by the cornea of each eye towards the single receiver element. Furthermore, the receiver assembly that receives the light reflected by the cornea may be formed by two receiver elements, each one of which is linked to one eye, each receiver element in this case being optically aligned with the direction of gaze of the respective eye thereof. The possibility of a set of lenses being arranged between the receiver assembly and the eyes has also been provided for.

The receiver assembly that receives the light reflected by the cornea may be formed by CCD or CMOS type electro-optical cameras or may be formed by CCD or CMOS type sensor arrays.

In one embodiment, the light emitter of the inspection system may be displaced and directed, in order to be able to emit light beams onto the cornea in different directions, in such a way that different geometric patterns of points where the beams of the light beams emitted on the cornea fall may be drawn (for example, straight lines, circumferences, etc.).

The system for tracking the direction of the gaze of the eyes and the inspection system may be made up of the same elements, such that there may be one single receiver for the light reflections produced on the cornea, the camera functioning as the receiver assembly, or vice versa, it only being possible for there to be one emitter, which emits light onto the cornea, emitting diffuse light, visible light, infra-red light or others, as necessary.

The method for measuring the topography and the thickness of the cornea comprises the following stages:

Sending diffuse light towards the cornea and capturing the light reflected on the cornea, in order to determine, via digital analysis techniques, the centre of rotation of the eyeball and the centre of the pupil of the eye, and obtain the direction of gaze of the eye, for example, as the line that joins the centre of rotation of the eyeball to the centre of the pupil.

Defining a virtual polar coordinates system, the coordinate origin of which coincides with the centre of the pupil.

Sending light beams towards the cornea and capturing the light points and bright spots, reflected by the cornea, linking each point and bright spot to the time at which it was captured.

Referencing information on the light points and bright spots on the virtual polar coordinates system, the coordinate origin of which coincides with the centre of the pupil, taking the position of the centre of the pupil at the time it was captured, determined by the direction of gaze at that time, into account.

Repeating the previous phases, taking the changes in the direction of gaze of the eye into account, until sufficient amount of data on light points and bright spots has been obtained, thus making it possible to obtain the topography and thickness of the cornea, by means of a number of statistical calculation algorithms based on spatial and temporal series.

As such, a low-cost device is obtained, which, given its constructive and functional characteristics, may preferably be used for the function for which it was designed, in relation to determining the topography and thickness of the cornea of the human eye, thus facilitating quick, simple analysis of the same, whilst avoiding causing patients irritation and discomfort.

DESCRIPTION OF THE DRAWINGS

FIG. 1 is a schematic representation of the components that form the apparatus of the invention for measuring the topography and thickness of the cornea.

FIG. 2 shows an illustrative example of a potential configuration of the apparatus of the invention for measuring the topography and thickness of the cornea.

DETAILED DESCRIPTION OF THE INVENTION

The apparatus of the invention for measuring the topography and thickness of the cornea is made up of a system for tracking (1) the direction of gaze (D) of the patient's eyes (2), a system for inspecting (3) the cornea (4) of the eyes (2), a system for displaying (13) visual stimuli in front of the eyes (2) and a computer (5, functionally connected to said tracking (1), inspection (3) and visual stimuli display (13) systems. The tracking system (1) makes it possible to instantly obtain the position of each eye (2) at all times, whilst the inspection system (3) makes the appropriate measurements, such that the computer (5) calculates the topography and thickness of the cornea (4) according to the information provided by both the tracking (1) and inspection (3) systems, regardless of the area in which the patient is fixing the direction of their gaze (D).

The system for tracking (1) the eyes' (2) direction of gaze includes a camera (6) and a diffuse light emitter (7) for each eye, in such a way that each diffuse light emitter (7) sends light to its respective eye (2), the reflection of which is captured by the corresponding camera (6), in order to determine the eyes' (2) direction of gaze. Furthermore, the system for inspecting (3) the cornea (4) comprises a light emitter (8) for each eye (2), which emits light beams (9) onto the cornea (4) and, a receiver assembly (10), which receives the light reflected by the cornea (4).

The system for displaying (13) visual stimuli may be formed of a number of screens, which display different optotypes or visual stimuli in front of the patient's eyes (2), thus making it possible to stimulate and guide the direction (D) of gaze of the patient's eyes (2), so as to expose different areas of the cornea (4), in such a way that the light emitter (8) of the inspection system (3) is provided with a greater area of cornea (4) on which to emit light information so that the computer (5) may subsequently calculate the topography and thickness of the cornea (4) more efficiently. Moreover, the possibility of the system (13) for displaying visual stimuli being formed by four LEDs positioned at strategic points close to the inner peripheral portion of the visual field of the eyes (2) has been provided for, in such a way that, via the selective emission of light by these LEDs, it is possible to stimulate and guide the direction of gaze (D) of the patient's eyes (2).

As such, in light of all of the above, the computer (5) controls the light emitters (7, 8) and the system (13) for displaying visual stimuli and processes all the information from each camera (6) and the receiver assembly (10), in order to determine the topography and thickness of the cornea (4) of each eye (2).

The light information sent onto the cornea (4) may adopt different shapes, such that the light emitter (8) of each eye (2) emits light beams (9) that draw multiple parallel or convergent lines or point clusters on to the cornea (4) point by point. As such, multiple lines with one or more converging points, multiple lines that cross at the central point of the pupil or at the apex of the corneal paraboloid, or multiple parallel lines may be physically displayed on the cornea (4). Multiple sets of parallel lines may also be displayed, in which all the sets of parallel lines converge at a same point, for example the centre of the pupil or the apex of the corneal paraboloid, where some sets of parallel lines converge at one single point, whilst other sets converge at one or more convergence points.

Based on the information obtained from the point cluster physically emitted onto the cornea (4) and via a numerical calculation on the computer (5), different patterns with predefined shapes, for example concentric discs, such as Placido discs, may be virtually displayed on the cornea (4).

In order to prevent potential interferences from affecting the measurement, the diffuse light emitter (7) of the tracking system (1) and the light emitter (8) of the inspection system (3) emit at different light frequencies, or emit at the same light frequency but in alternating periods of time.

The light emitter (8) that emits light beams (9) onto the cornea (4) may be an infra-red light, a collimated light or a laser light emitter. In a potential configuration, it may be an emitter that emits thin light beams, such that the maximum dimension of the cross-section of the beam sent towards a point close to the cornea (4) is less than the minimum height between the peaks and valleys of the stratified cross-section of the cornea (4) to be measured.

In the diagram shown in FIG. 1, it is possible to observe how the receiver assembly (10) that receives light reflected by the cornea (4) is formed by two receiver elements, each one of which is linked to one of the patient's eyes (2), such that each receiver element is optically aligned to the direction of gaze (D) of the respective eye (2) thereof to be analysed.

The possibility of the receiver assembly (10) receiving the light reflected by the cornea (4) being formed by a single receiver element common to both eyes (2) has been provided for, in which case the single receiver element is not aligned with the direction of gaze (D) of the eyes (2) to be analysed, meaning that in order to optically align it with each eye (2) a set of directed mirrors (12) is used, which direct the light reflected by the cornea (4) of each eye (2) towards the single receiver element. The illustrative example shown in FIG. 2 represents a potential embodiment of the set of mirrors (12), in which a single eye (2) has been represented for the purposes of clarity. Likewise, the set of mirrors (12) may be used to direct the light beams (9) sent by the light emitter (8) towards the cornea (4).

The possibility of a set of lenses (11) being arranged between the receiver assembly (10) and the eyes (2) has been provided for. As such, in the case of there being one single receiver element, one or more lenses are arranged between said single receiver element and the patient's eyes (2) and, in the event of there being a receiver element for each eye (2), one or more lenses are arranged between each receiver element and the patient's respective eye (2).

The receiver assembly (10) that receives the light reflected by the cornea (4) may be formed by CCD or CMOS type electro-optical cameras, such that the receiver assembly (10) may be made up of two CCD or CMOS type electro-optical cameras, each one linked to one of the patient's eyes (2), or one single CCD or CMOS type electro-optical camera, linked to both of the patient's eyes (2). It has also been provided for that the receiver assembly (10) may be formed of CCD or CMOS type sensor arrays, such that, in this case, the receiver assembly (10) may be made up of a single CCD or CMOS type sensor array, linked to both of the patient's eyes (2), or by two CCD or CMOS type sensor arrays, each one linked to one of the patient's eyes (2).

In one embodiment, each sensor array is flat in shape and is located perpendicularly to the optical axis corresponding to the direction of gaze (D) of the eye (2) to which it is linked. According to another embodiment, each sensor array is formed by a flat surface perpendicular to the optical axis corresponding to the direction of gaze (D) of the eye (2) to which it is linked and a cylindrical surface arranged around and at a certain distance from the eye (2), the axis of the cylindrical surface being aligned with the direction of gaze (D) of the eye (2). In another embodiment, each sensor array is arranged around and at a certain distance from the eye (2), thus forming a spherical or parabolic dome.

A possible embodiment of the invention provides that the light emitter (8) of the inspection system (3) may be displaced and directed, in order to emit light beams (9) onto the cornea (4) in different directions and thus be able to draw geometric patterns of points where the beam falls on the cornea (4) (for example, straight lines, circumferences, etc.).

The system for tracking (1) the direction of gaze (D) of the eyes (2) and the inspection system (3) may be made up of the same elements, such that there may be one single element that receives the light reflections produced on the cornea (4), the camera functioning as the receiver assembly (10), or to the contrary, there may be one single emitter element, which emits light onto the cornea (4), emitting diffuse light, visible light, infra-red light or others, as necessary.

As such, in view of all of the above, the computer (5), which is functionally connected to the light emitters (7,8) and to the receiver assembly (10), is able to control the direction of each light beam (9) sent and to capture the instantaneous position of each eye (2), the instantaneous position of the reflections of each light beam (9) on the cornea (4) and/or the shape of the light points reflected, in such a way that the computer (5), via numerical calculation and based on the iterative analysis of the angles of incidence and reflection of the light beams (9) emitted and the reflections captured, is able to calculate the topography of the cornea (4), of both of the outer layer and the inner layer thereof, as well as the thickness of the same along the length and width of its span.

The method for measuring used to determine the topography of the cornea (4), as well as the thickness thereof along the length and width of the same, comprises the following stages (the description is carried out based on just one of the patient's eyes (2)):

The direction of gaze (D) of the patient's eye (2) is firstly determined, the centre of rotation of the eyeball and the centre of the pupil thus being calculated, the direction of gaze (D) being the line that joins the centre of rotation of the eyeball and the centre of the pupil.

The direction of gaze (D) is determined using the tracking system (1), the surface of the cornea (4) of the eye (2) thus being illuminated via the diffuse light emitter (7). The camera (6) subsequently captures the light reflected by the cornea (4) and the computer (5), by means of a piece of automatic shape recognition software, in order to obtain the apparent geometry of the pupil, the apparent geometry of the eyeball (which corresponds to a spheroid) and/or the apparent geometry of the cornea (which corresponds to a paraboloid). Once this information has been obtained from the eye (2), the centre of rotation of the eyeball and the centre of the pupil is calculated, and based on this information, the direction of gaze (D) of the eye (2).

The direction of gaze (D) is determined by means of a technique known as "eyes-tracking", based on the recognition of the changes in the position of corneal reflections produced by diffuse illuminators or by changes in the apparent geometry of the pupil. As such, the same shall not be described in detail, given that it does not fall within the scope of the invention.

A virtual polar coordinates system is secondly defined, the coordinate origin of which coincides with the centre of the pupil calculated in the previous phase. In order to do so, the image of the cornea (4) surface captured by the inspection system (3) is represented on the virtual polar coordinate system, in such a way that the topography and thickness of the cornea (4) may be measured, regardless of the area in which the patient is fixing their gaze, since the reference system on which the captured image is displayed does not have a fixed coordinate origin but is rather relative, according to the patient's direction of gaze direction (D).

Thirdly, light beams (9) are sent towards the cornea (4) from the light emitter (8) of the inspection system (3), in such a way that the light points and bright spots reflected on the surface of the cornea (4), on the outer or inner layers thereof, are captured by the receiver assembly (10) of the inspection system (3).

Each light point and bright spot is linked to the time at which it was captured, in such a way that when the topography of the cornea is reconstructed, the position of the pupil centre at the time it was captured is taken into account, determined by the direction of gaze (D) of the eyes (2) at that moment.

The diffuse light emitter (7) of the tracking system (1) and the light emitter (8) of the inspection system (3), may emit simultaneously when the emissions are produced at different light frequencies, in which case the cameras (6) and the receiver assembly (10) are appropriately configured to distinguish the light frequencies necessary. In the event of both light emitters (7, 8) emitting at the same light frequency, the diffuse light emission from the diffuse light emitter (7) is interrupted and light beams (9) are sent towards the cornea (4) from the light emitter (8) of the inspection system (3).

In a fourth step, the information obtained from the light points and bright spots, captured by the receiver assembly (10) of the inspection system (3), is referenced on the previously defined polar coordinates system, with which information is obtained on the cornea (4) depending on the patient's direction of gaze (D). In other words, the information is referenced relative to the centre of the pupil of the patient's eye (2).

In a fifth step, the previous phases are repeated according to changes in the direction of gaze (D) of the patient's eye (2), up until the point where enough points are obtained (for example, points captured per $mm^2$ of cornea). The eye movements and the subsequent changes in the patient's direction of gaze (D) make it possible to expose different areas of the cornea (4) to the light beams (9), the reflections of which are to be captured.

As such, each time the patient diverts their gaze, the virtual polar coordinates system is re-referenced with the new position of the centre of the pupil and information is once again captured from the cornea (4) by means of the inspection system (3), this iterative process being repeated until enough data on light points and bright spots is obtained, which makes it possible to obtain the topography and thickness of the cornea (4).

In addition, a number of dynamic optotypes or visual stimuli may be displayed whilst capturing information from the cornea (4), which are presented in front of the patient's eyes (2) via the screens or the LEDs of the system for displaying visual stimuli (13). As such, it is possible to stimulate and guide the direction of gaze (D) of the patient's eyes (2), in order to expose areas of the cornea to be measured in an appropriate position so that the light beams (9) emitted by the light emitter (8) fall onto it at the desired angle. The dynamic optotypes may be displayed on the screens (13), moving at a constant distance from the patient (i.e., on the plane perpendicular to their primary gaze position) or, in cooperation with a mobile monofocal or varifocal lens, at a variable distance (i.e., at different depths in the three-dimensional virtual environment).

Finally, when sufficient information on light points and bright spots of the cornea (4) has been obtained, a topographic map of the cornea (4) is obtained via a number of statistical calculation algorithms based on spatial and temporal series that process the information of said light points and bright spots.

The topographic map of the cornea (4) is reconstructed using conventional processing techniques, based on the geometric difference between the location of a real reflected point and a theoretical reflected point on a perfect reference figure, which is usually a sphere or a paraboloid. As such, the real information obtained from the light points and bright spots is compared to a number of theoretical light points and bright spots obtained from the reflection on a perfectly spherical reflective surface, in such a way that, by means of this comparison, it is possible to construct a topographic survey of the cornea (4) and, where appropriate, detect anomalies in the cornea (4) analysed.

The invention claimed is:

1. A piece of apparatus for measuring the topography and the thickness of the cornea, comprising a system for tracking the direction of gaze (D) of the eyes, including a camera and a diffuse light emitter for each eye; a system for inspecting the cornea, comprising a light emitter for each eye, which emits light beams onto the cornea and a receiver assembly, which receives the light reflected by the cornea; a system for displaying visual stimuli in front of the eyes and; a computer that controls the light emitters and the system for displaying visual stimuli, which also processes the information from each camera and the receiver assembly in order to determine the topography and thickness of the cornea of each eye.

2. The apparatus for measuring the topography and thickness of the cornea according to claim 1, wherein the system for displaying visual stimuli is formed by a number of image display screens, which guide the direction of gaze (D) of the patient's eyes.

3. The apparatus for measuring the topography and thickness of the cornea according to claim 1, wherein the system for displaying visual stimuli is formed by four LEDs positioned at strategic points close to the inner peripheral portion of the visual field of the eyes.

4. The apparatus for measuring the topography and thickness of the cornea according to claim 1, wherein light emitter of each eye emits light beams, displaying multiple parallel lines on the cornea.

5. The apparatus for measuring the topography and thickness of the cornea according to claim 1, wherein light emitter of each eye emits light beams, displaying multiple convergent lines on the cornea.

6. The apparatus for measuring the topography and thickness of the cornea according to claim 1, wherein the light emitter of each eye emits light beams, displaying point clusters on the cornea.

7. The apparatus for measuring the topography and thickness of the cornea according to claim 1, wherein the light emitters emit at different light frequencies.

8. The apparatus for measuring the topography and thickness of the cornea according to claim 1, wherein the light emitters emit at the same light frequency, however do so in alternating periods of time.

9. The apparatus for measuring the topography and thickness of the cornea according to claim 1, wherein a set of lenses is arranged between the receiver assembly and the eyes.

10. The apparatus for measuring the topography and thickness of the cornea according to claim 1, wherein the receiver assembly that receives the light reflected by the cornea is formed by a single receiver element common to both eyes, a set of directed mirrors being used to direct the light reflected by the cornea of each eye towards the single receiver element.

11. The apparatus for measuring the topography and thickness of the cornea according to claim 1, wherein the receiver assembly that receives the light reflected by the cornea is formed of two receiver elements, each one linked to an eye, each receiver element being optically aligned with the direction of gaze (D) of the respective eye thereof.

12. The apparatus for measuring the topography and thickness of the cornea according to claim 1, wherein the receiver assembly that receives the light reflected by the cornea is formed by CCD or CMOS type electro-optical cameras.

13. The apparatus for measuring the topography and thickness of the cornea according to claim 1, wherein the receiver assembly that receives the light reflected by the cornea is formed of CCD or CMOS type sensor arrays.

14. The apparatus for measuring the topography and thickness of the cornea according to claim 13, wherein each sensor array is flat in shape and is located perpendicularly to the optical axis corresponding to the direction of gaze (D) of the eye to which it is linked.

15. The apparatus for measuring the topography and thickness of the cornea according to claim 13, wherein each sensor array is formed by a flat surface perpendicular to the optical axis corresponding to the direction of gaze (D) of the eye to which it is linked and a cylindrical surface, arranged around and at a certain distance from the eye, the axis of the cylindrical surface being aligned with the eye's direction of gaze (D).

16. The apparatus for measuring the topography and thickness of the cornea according to claim 13, wherein each sensor array is arranged around and at a certain distance from the eye, forming a spherical or parabolic dome.

17. The apparatus for measuring the topography and thickness of the cornea according to claim 1, wherein the light emitter of the inspection system may be displaced and directed, in order to emit light beams onto the cornea in different directions.

18. A method for measuring the topography and thickness of the cornea using the apparatus of claim 1, comprising the stages:
   Sending diffuse light towards the cornea and capturing the light reflected on the cornea in order to determine, via digital analysis techniques, the centre of rotation of the eyeball and the centre of the pupil of the eye and to obtain the direction of gaze (D) of the eye as the line that joins the centre of rotation of the eyeball to the centre of the pupil;
   Defining a virtual polar coordinates system, the coordinate origin of which coincides with the centre of the pupil;
   Sending light beams towards the cornea and capturing the light points and bright spots reflected by the cornea, linking each light point and bright spot to the time at which it was captured;
   Referencing the information on the light points and bright spots on the virtual polar coordinates system, the coordinate origin of which coincides with the centre of the pupil;
   Repeating the above stages, taking the changes in the eye's direction of gaze (D) into account, until enough data on light points and bright spots has been obtained; and
   Obtaining a topographic map of the cornea through a number of statistical calculation algorithms based on spatial and temporal series, which process the information on the light points and bright spots.

19. The method for measuring the topography and thickness of the cornea according to claim 18, wherein the diffuse light and the light beams sent towards the cornea are emitted simultaneously at different light frequencies.

20. The method for measuring the topography and thickness of the cornea according to claim 18, wherein the diffuse light and the light beams sent towards the cornea are emitted at the same light frequency in alternating periods of time.

21. The method for measuring the topography and thickness of the cornea according to claim 18, wherein a number of dynamic optotypes, which stimulate the patient in order to direct the direction of gaze (D) of their eyes towards a desired position, are displayed on a number of screens, arranged in front of the patient's eyes.

22. The method for measuring the topography and thickness of the cornea, according to claim 18, wherein by means of a number of LEDs arranged in front of the patient's eyes, a number of lights that stimulate the patient are emitted, in order to direct the direction of gaze (D) of their eyes towards a desired position.

23. The method for measuring the topography and thickness of the cornea according to claim 18, wherein light beams are sent onto the cornea and the light points reflected by the outer layer and the inner layer of the cornea are captured.

* * * * *